United States Patent [19]
Becker et al.

[11] Patent Number: 5,983,238
[45] Date of Patent: Nov. 9, 1999

[54] GEMSTONS IDENTIFICATION TRACKING AND RECOVERY SYSTEM

[75] Inventors: Seth P. Becker, Farmington; Paul J. Becker; Scott E. Becker, both of West Hartford; Paul V. Lombardo, Farmington, all of Conn.

[73] Assignee: Diamond ID, West Hartford, Conn.

[21] Appl. No.: 08/998,525

[22] Filed: Dec. 26, 1997

[51] Int. Cl.⁶ ........................................................ G06F 17/30
[52] U.S. Cl. .............................. 707/104; 707/1; 707/3; 707/10
[58] Field of Search ................ 707/3, 4, 5, 6.1, 707/100, 101, 104; 705/28, 402, 2, 35; 395/200.31; 380/25, 51; 233/81; 235/383; 340/551, 825.31; 382/126, 137; 376/164

[56] References Cited

U.S. PATENT DOCUMENTS

| | | |
|---|---|---|
| D. 330,873 | 11/1992 | Kaplan ........................................ D11/90 |
| 2,293,100 | 8/1942 | Baumgold .................................... 125/1 |
| 2,909,961 | 10/1959 | Sammuels, Sr. . | 
| 3,947,120 | 3/1976 | Bar-Issac et al. . |
| 4,125,770 | 11/1978 | Lang . |
| 4,177,466 | 12/1979 | Reagan . |
| 4,392,476 | 7/1983 | Gresser et al. ......................... 125/30 R |
| 4,401,876 | 8/1983 | Cooper .............................. 219/121 LJ |
| 4,467,172 | 8/1984 | Ehrenwald et al. ............. 219/121 LH |
| 4,732,867 | 3/1988 | Schnable ................................... 437/22 |
| 4,749,847 | 6/1988 | Despres . |
| 4,818,998 | 4/1989 | Apsell et al. . |
| 4,893,840 | 1/1990 | Berkowitz ................................. 283/81 |
| 4,900,147 | 2/1990 | Bowley et al. . |
| 4,908,629 | 3/1990 | Apsell et al. . |
| 5,124,935 | 6/1992 | Wallner et al. . |
| 5,149,938 | 9/1992 | Winston et al. .................... 219/121.69 |
| 5,379,102 | 1/1995 | Takeuchi . |
| 5,410,125 | 4/1995 | Winston et al. .................... 219/121.69 |
| 5,426,282 | 6/1995 | Humble .................................... 235/383 |
| 5,483,038 | 1/1996 | Ota et al. ........................... 219/121.69 |
| 5,504,303 | 4/1996 | Nagy .................................. 219/121.68 |
| 5,573,684 | 11/1996 | Winston et al. .................... 219/121.85 |
| 5,615,508 | 4/1997 | Bain ........................................... 705/28 |
| 5,659,741 | 8/1997 | Eberhardt ................................ 707/104 |
| 5,671,412 | 9/1997 | Christiano .............................. 707/104 |
| 5,777,884 | 7/1998 | Belka ................................. 364/478.13 |

FOREIGN PATENT DOCUMENTS 2 215 041   9/1989   United Kingdom .

OTHER PUBLICATIONS

Avram Piltch, *Hi–Tech Gem Identification Improves Security,* Electronic Media Editor, Web posted: Aug. 1, 1997, Appears in Jul. 16, 1997 Issue, pp. 1–4.

*Who's Who in Brand Name & Ideal Cut Diamonds,* May 1998 Issue of Modern Jeweler, starting on pp. 60–65.

*Primary Examiner*—Paul R. Lintz
*Assistant Examiner*—Diane D. Mizrahi
*Attorney, Agent, or Firm*—Cantor Colburn LLP

[57] ABSTRACT

An identification, tracking and recovery system includes a central database for electronically storing unique and relevant information of a plurality of gemstones to assist with the recovery of lost or stolen gemstones. The information of each gemstone is stored as a gemstone entry in the database which includes the characteristics of the gemstone, a unique identification number inscribed into a surface of the gemstone by a laser, and personal information of the owner of the gemstone. A user interface enables a user to communicate with a processor which stores and retrieves the relevant information from the database in accordance with an algorithm. The user interface may be located remotely from the database which is located at a central headquarters. The processor is capable of cross-referencing the information of the stored gemstone entry to enable retrieval of a gemstone entry based on any known information, such as the diamond identification number and information pertaining to owner of the gemstone. In addition, the user may flag the gemstone entry of a lost or stolen gemstone to easily identify the status of the ownership of the gemstone and also enable the system. The flagged gemstone entries may then be retrieved to generate a report that lists all of the lost or stolen gemstones stored in the database.

40 Claims, 8 Drawing Sheets

DIAMOND INFORMATION

DIAMOND ID # [ ]   SUPPLEMENTAL CERT. # [ ]
SOURCE OF CERTIFICATE [ ]   CETIFICATE DATE [ ]

SHAPE AND CUT
- MEASUREMENTS [ ]
- WEIGHT [ ]

FINISH
- POLISH [ ]
- SYMMETRY [ ]

CLARITY GRADE [ ]
COLOR GRADE [ ]
FLUORESCENCE [ ]

PROPORTIONS
- DEPTH [ ]
- TABLE [ ]
- GIRDLE [ ]
- OUTLET [ ]
- IDEAL CUT [YES] [NO]

TOTAL ESTIMATED RETAIL REPLACEMET VALUE
[ ]

ENTER [ ]   OTHER [ ]

FIG. 11

ENTER PERSONAL INFORMATION

DIAMOND ID # [ ]   SUPPLEMENTAL CERT # [ ]

FIRST NAME [ ]   M [ ]   LAST NAME [ ]

NUMBER [ ] [ ] [ ]   E MAIL [ ]

CITY [ ]   ST [ ]   ZIP [ ]

HOME PHONE [ ]   SOCIAL SECURITY NUMBER [ ]   LIC. #/I.d. # [ ]

WORK PHONE [ ]   FAX [ ]

CELLULAR PHONE [ ]   PAGER [ ]

INSURANCE COMPANY [ ]   INSURANCE AGENT [ ]   [ENTER]

GEMSTONS IDENTIFICATION TRACKING AND RECOVERY SYSTEM

BACKGROUND OF THE INVENTION

1. Field of the Invention

The present invention relates to a tracking and recovery system and more particularly to a gemstone identification, tracking and recovery system including a database for storing the characteristics of a gemstone, a unique identification number and personal information of the owner of the gemstone to enable a user to cross-reference this information, and identify and track the ownership of the gemstone or provide information about the gemstone to aid with the recovery of the gemstone should it become stolen or lost.

2. Description of the Related Art

In the case of precious gemstones such as diamonds, there exists a need for a simple, reliable method by which the identity of a gemstone can be determined to enable the gemstone to be recovered if lost or stolen. The most common problem with recovering a gemstone is accurately identifying the gemstone. Even if the gemstone is known to be stolen or lost, the finder of the gemstone must be able to accurately identify its owner. This problem is of particular concern to insurance companies, in that gemstones are often insured and it has been difficult to identify the stolen gemstone even if it is recovered. Insurance companies in the past have also been subject to fraudulent claims. Furthermore, police often request jewelers to identify gemstones to help the police resolve cases and typically the jeweler can be of no assistance because there is no easy way to accurately identify the gemstone.

A system that assists with the identification, tracking and recovery of the gemstone is would significantly reduce the trade of stolen gemstones and therefore, would be of great interest to insurance companies, police departments, jewelers and purchasers which all have an interest in recovering stolen or lost gemstones. Such a system would also greatly increase consumer confidence in the trade of gemstones. Despite various methods of identifying and tracking gemstones, the recovery of gemstones still remains a problem.

A number of methods of identifying a gemstone are currently available. One such method, shown in U.S. Pat. No. 5,124,935 to Wallner et al., includes a system for providing an optical fingerprint of a gemstone whereby a laser beam is focused onto a gemstone and its optical response is recorded onto a recording medium, preferably a photographic medium. This system provides a unique fingerprint of the gemstone which is reproducible and provides sufficient proof to identify a gemstone. However, the device that generates the optical fingerprint is very complex and expensive to manufacture. For this system to be effective, it would require an optical device to be placed at every location that need to identify a gemstone, such as police stations and jewelry stores. Even if a jeweler had this optical device, it would be the jeweler's responsibility to record all optical fingerprints before the gemstones left the store in order for the system to be effective. This system is not, however, practical considering the cost of each device and extra personnel, time and training needed to operate the optical devices. In the alternative the gemstone may be delivered to a facility for optical scanning. Even after generating an optical fingerprint, an expert is still required to analyze the optical fingerprint with others on file to identify the owner of the gemstone. Either way this method is not conducive to easily identifying and matching a missing gemstone to its owner.

Another method of identifying gemstones is the use of X-ray topography to generate a unique fingerprint of the gemstone. This method is also very complex and expensive to manufacture, and requires an expert to evaluate and compare the fingerprint to other recorded fingerprints to verify the identity of the gemstone.

Another method of identifying a gemstone is the etching of a number or other indicia onto a surface of the gemstone using a laser. The number is inscribed small enough so as to not detract from the quality or brilliance of the gemstone, but can be easily "read" with a common magnifying tool used by jewelers, police, gemstone purchasers and insurance companies.

Once the gemstone can be uniquely identifiable, a holder of a lost or stolen gem requires a method of determining the owner of the identified gemstone. U.S. Pat. No. 5,124,935 to Wallner et al. shows a gemstone identifying and tracking system that stores optical fingerprints of stolen gemstones in a central database. Gemstones that are reported to the central database as being stolen or lost are then compared electronically using software to match the fingerprint of the stolen or lost gemstone to its records of fingerprints of gemstones reported as stolen or lost. The software then narrows the possible matches of the stolen gemstone to a small number of fingerprints. An expert then analyzes the results and provides an opinion of which fingerprint is an identical match. The need of an expert to positively identify the gemstone as stolen or lost and the need for an optical device at each jeweler store and police station renders this system impractical for wide spread use.

SUMMARY OF THE INVENTION

The above-discussed and other drawbacks and deficiencies of the prior art are overcome or alleviated by the gemstone identification, tracking and recovery system of the invention.

According to the present invention there is provided a system for identifying, tracking and recovering of lost or stolen gemstones. The system includes a database for electronically storing a plurality of gemstone entries that include unique and relevant information of each corresponding gemstone. The stored information includes indicia unique to each gemstone and personal information of the owner of the gemstone. Preferably the information also includes the characteristics of the gemstone, the insurer of the gemstone and the store where the gemstone was purchased. Each diamond is uniquely identified by indicia inscribed into a surface of each of the gemstones. A user interface displays the gemstone entries received from the database and permits the user to provide the relevant information of the gemstone for storage in the database. A processor, in accordance with an algorithm, retrieves and stores the gemstone entries, requested and provided by the user at the user interface, from the database. Preferably, the processor cross-references the indicia and/or characteristics of the gemstone to personal information of the owner. The processor also stores the relevant information of the gemstone provided, at the user interface, in the database. In addition, the processor may flag a gemstone entry in accordance with the status of ownership of the gemstone provided by the user interface.

An object of the present invention is to provide a gemstone identification, tracking and recovery system having a central database for storing information of gemstones and their owners, wherein the gemstone has unique indicia inscribed in a side surface of the gemstone to permit anyone to easily identify the gemstone and thereby eliminate any need for complex and expensive apparatus to identify the gemstone.

Another object of the present invention is to provide a gemstone identification, tracking and recovery system having a central database for storing information of gemstones and their owners, wherein the system is capable of searching and cross-referencing known information of the gemstone or owner to identify both the characteristics of the gemstone and its owner for easily tracking a lost or missing gemstone to its rightful owner.

Another object of the present invention is to provide a gemstone identification, tracking and recovery system having a central database for storing information of gemstones and their owners, wherein the status of the ownership of the gemstone may be easily changed between missing and found and therefore, made available quickly to interested parties such as the police, insurance companies, jewelers and purchasers.

Another object of the present invention is to provide a gemstone identification, tracking and recovery system having a central database for storing information of gemstones and their owners, wherein the gemstones are laser inscribed with unique indicia to enable personal verification of the gemstone and provide greater quality control.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGS..

DETAILED DESCRIPTION OF THE INVENTION

Figure 1:
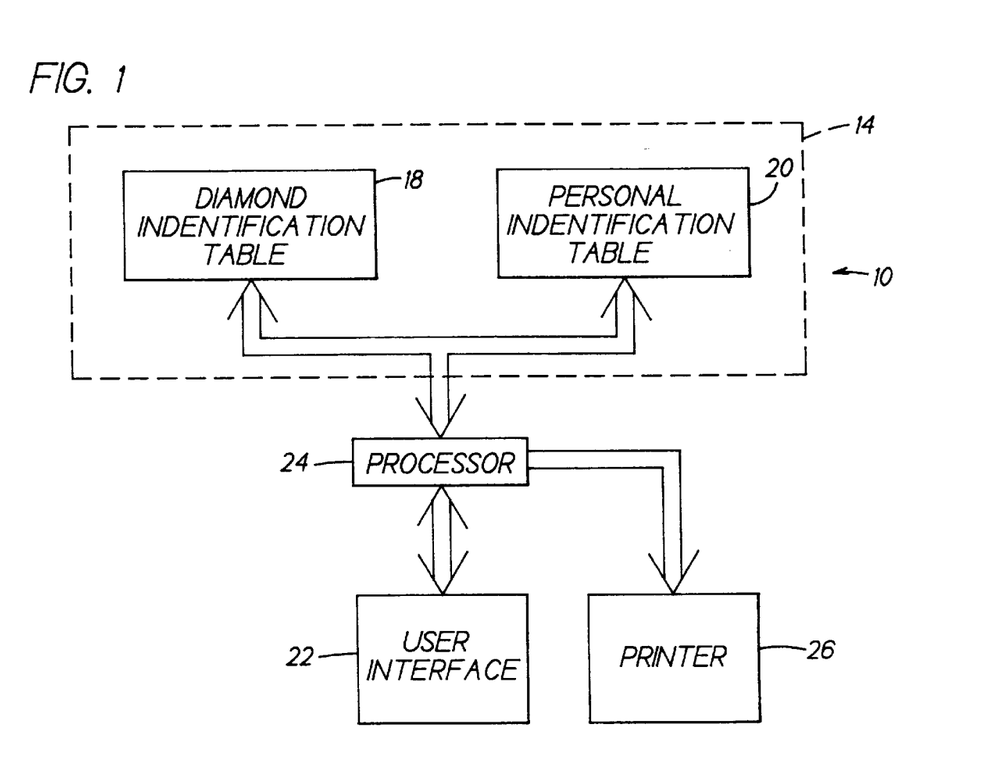
FIG. 1 is a block diagram of a gemstone identification, tracking and recovery system of the type embodying the present invention.

In FIG. 1, there is a gemstone identification, tracking and recovery system, generally designated 10, that provides a central depository of relevant information of a purchased gemstone that can be used to identify a stolen or lost gemstone 12 (see FIG. 2) to aid with the recover of the gemstone. The recovery system 10 includes a central database 14 that electronically stores the gemstone information and enables a system user located at a central headquarters to access the stored information to determine whether the gemstone is lost or stolen. This central headquarters would be the dependent party for recovering lost or stolen gemstones which would assist the precious stone purchasing market. A third party, such as the police, insurance companies, store owners, and gemstone owners may contact the central headquarters to inquire about information relating to a gemstone's owner or its characteristics, as well as receive periodic reports from the headquarters listing missing or found gemstones. The centralization of this information between these third parties also increases the odds of recovery of the gemstone. In an alternative these third parties may search remotely the database to find information relating to a particular gemstone, provided they have the proper level of access. While the recovery system of the present invention may be used for all gemstones, the recovery system 10 is particularly relevant with respect to diamonds and therefore, hereinafter, the recovery system will be described with respect to the identification, tracking and recovery of diamonds.

Figure 2:
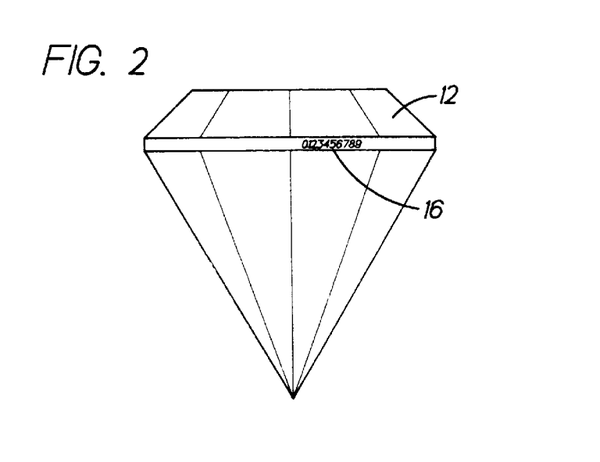
FIG. 2 is a side elevational view of a gemstone having an identification number etched into a side surface of the gemstone.

The information for each diamond 12 is stored in the database 14 as a diamond entry which includes information of the characteristics of the diamond 12 and personal information of the owner of the diamond. The recovery system 10 also identifies the ownership status of the diamond as being stolen/lost if the owner claims the diamond to be missing. As shown in FIG. 2, the diamonds 12 are uniquely identified by indicia or an identification number 16 etched permanently into a surface of the diamond by a laser. The permanent identification is especially important in the case of a product whose quality and value can only be determined by specially skilled experts. The identification number 16 is used as the primary identifier for the information stored in the database 14. When a diamond is reported stolen or lost, the recovery system 10 flags the corresponding stored diamond entry which enables the user to easily cross-reference a lost or stolen diamond to its owner. The system may also establish a protocol in that the change of the lost/stolen status of a gemstone may only be entered after an official police report has been filed.

The characteristics of the diamond 12 stored in the database 14 generally include the information that is typically found in a diamond certificate issued by a certified diamond grading laboratory such as the Gemological Institution of America (G.I.A) and the International Gemological Institute (I.G.I). The typical information in a diamond certificate includes the diamond identification number 16 etched into the diamond 12, the source of the certification, the date of certification and the physical characteristics of the diamond, such as its shape, cut, proportions, finish and other factors. The typical personal information of the diamond owner includes the owner's name, address, home phone number, work phone number, social security number, e-mail address, facsimile number, cellular phone number, pager, the insurance company insuring the diamond, name of insurance agent and other relevant information. Additional personal information may include the name, address, telephone number, facsimile number and other relevant information of the store where the diamond was purchased.

The diamond entries stored in the database 14 may be updated or have new information added thereto. The recovery system 10 also includes the capability of recording the history of the transfer of ownership of the diamond. The recovery system also generates reports that list lost/stolen diamonds and/or list diamonds insured by a specific insurance company. It can be appreciated that any report may be generated by any piece of information used to identify the diamond, such as the owner's name and any physical characteristic of the diamond.

Referring to FIG. 1, the database 14 includes a table 18 for storing the information relating to the characteristics of the diamond and another table 20 for storing the personal information of the diamond owner. Each table 18, 20 stores the diamond identification number 16 and the supplemental certificate number for each diamond entry to provide a common a link to the corresponding diamond and owner information. The system user enters the diamond and personal information of the diamond entry to the database 14 through a graphical user interface 22. In a preferred embodiment, the user interface includes a monitor, keyboard and a mouse. A processor 24 receives, manipulates and stores the information into the database in accordance with a software program or algorithm 25. When a search for the diamond and personal information is performed, the processor searches the database in accordance with the parameters of the search request and retrieves the selected diamond entry to the user interface 22. The retrieved diamond entry may then be provided to a printer 26. The retrieval of the selected diamond entry is performed by cross-referencing the information in the tables 18, 20. This ability to cross-reference these parameters allows, for example, personal information to be retrieved by entering the diamond identification number, and vice versa.

The gem labs are a third party that grade the diamonds 12 for retailers and diamond vendors, who sell diamonds to retailers. The gem labs issue a diamond certificate that define the characteristics and quality of the diamond. The diamond certificate further includes a primary certificate number that matches the identification number inscribed on the diamond. This feature reduces the likelihood of fraud or misrepresentation of the quality of the diamond by enabling a purchaser to personally and easily verify that the inscribed identification number of the diamond matches or is bonded to the diamond certificate number before finally leaving the store. In the past diamond certificates were not widely used, however, nowadays most diamonds sold include a diamond certificate. These gem labs also have the capability to laser inscribe the unique identification number 16 onto a surface of the diamonds 12. Presently, only a small percentage of diamonds on the market have this identification number laser inscription, however, it is envisioned that a growing percentage of the diamonds will be inscribed to take advantage of the present recovery system.

Laser inscribing of diamonds by the gem lab is desirable and advantageous for consumers, diamond vendors and jewelers. The inscription and certification of the diamond by the gem lab provides unbiased factual statement of the diamonds quality and characteristics. This identification of the diamond prevents misrepresentation of the quality of the diamond by retailers and vendors. This method of identifying the diamonds also automatically provides the identity of the gemstone to the purchaser and does not require any extra measures to be taken by jewelers. In general, diamonds having a laser inscription identification numbers permits the diamond to be easily and quickly identified by the owner, police, insurance companies, and jewelers without the need for an optical device located at each jewelry store and police station. The simple, easily identifiable number on the diamond, which is inscribed by an independent party, greatly reduces the margin of error of incorrectly identifying the diamond. Furthermore, the serial numbered diamonds and recovery system may be easily integrated with a police computer network for recovering lost or stolen items.

The most common method of inscribing a diamond 12 is by burning the unique identification number 16 into a side surface of the diamond. A diamond is comprised of approximately 99.95% carbon and laser burns the carbon which, then turns black in color making the identification number 16 visible. The inscribed identification number is undetectable to the naked eye and therefore does not interfere with the quality, value, aesthetics and brilliance of the diamond. Moreover, the identification number 16 can be "read" easily by a jeweler, police and a diamond purchaser using a 10× magnifying glass or loupe.

The information stored in the database 14 may be provided by the store owner at the time of purchase or preferably, by the purchaser of the diamond 12 at their convenience. To register the diamond in the database, the diamond purchaser would provide to the central headquarters the characteristics of the diamond listed on the diamond certificate and the personal information of the purchaser or owner. In an alternative, the gem labs may issue a second diamond certificate for registering the diamond 12 in the database 14. The second certificate would include a detachable portion that includes the information typically found on a diamond certificate and a questionnaire that the purchaser fills out to provide the personal information. To register the diamond, the owner simply completes the questionnaire, detaches this portion from the second diamond certificate, and sends the detachable portion to the central headquarters for registration. This personal information provided by the owner may be updated annually. The second certificate may also include a supplemental certificate number which is different from the identification number of the diamond. This supplemental certificate number may be used to search and cross-reference the information stored in the database.

Referring to the flow diagrams of algorithm 25 of FIGS. 3–7, the system user or authorized third party, i.e. police, jeweler, insurance company and owners, first logs onto the recovery system 10, as shown in block 30. Preferably, only personnel located at the central headquarters have access to the recovery system. FIG. 8 illustrates the graphical display or window 31 that the user interface provides to the system user at the time of log on. A user name and a password must be entered by the system user to safeguard the system and prevent unauthorized personnel from having access to the recovery system 10. The recovery system also may limit the access or options available to a particular user. For example, an insurance company may only have access to request and print out a report of stolen diamonds, and detailed data of diamonds that are insured by their company. The police, on the other hand, may have access to all information on the database 14, and the ability to change the status of the diamond entry to stolen, lost or found. In this case, the police, insurance company, jeweler or owner would contact the central headquarters to change or request information.

Figure 9:
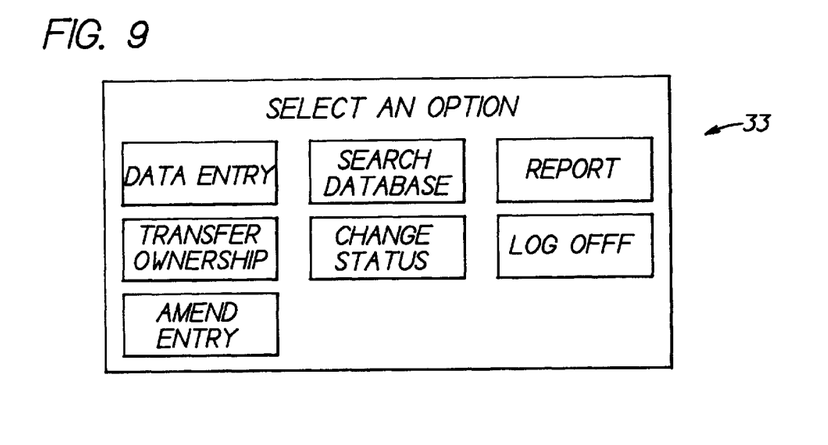
FIG. 9 is a graphical window of the recovery system of FIG. 1 displayed to a system user at block 32 of FIG. 3.

After the user is logged onto the system 10, the user, as shown in block 32, has the option of selecting a desired action at a main menu of window 33, as shown in FIG. 9. The main menu prompts the system user to select the options of entering the information of a new diamond, recording the transfer of a diamond entry, amending the database of a diamond entry, searching the database of a diamond entry, changing the status of a diamond entry, generating a report of the selected diamond entries, and logging off the system.

Figure 10:
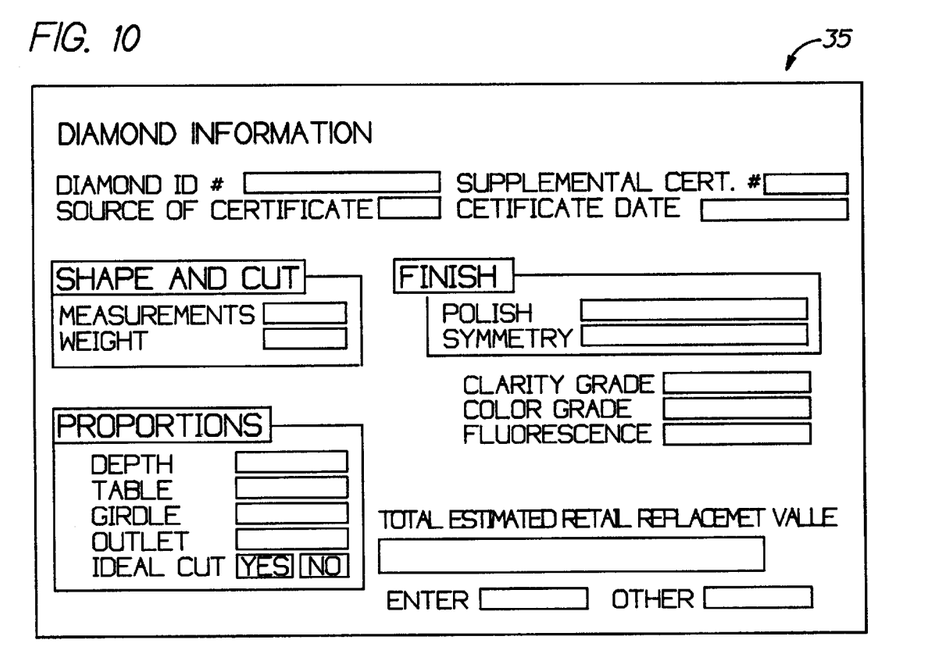
FIG. 10 is a graphical window of the recovery system of FIG. 1 displayed to a system user at block 34 of FIG. 3.

When "Data Entry" is selected in window 33 of FIG. 9, the user enters the information relating to the characteristics of the diamond provided by the diamond certificate. In block 34, the information that may be entered into the database, but not limited to, as shown in window 35 of FIG. 10, is the diamond identification number 16, the supplemental diamond certificate number, the source of the certificate, the date of certification, the shape and cut of the diamonds (namely the measurements and weight), the proportions of the diamond (namely, the depth, table, girdle, culet, ideal cut, crown angle\crown height and pavilion angle\pavilion depth), the finish of the diamond (namely, the polish and symmetry), the clarity grade, the color grade, the florescence, any comments, total estimated retail replacement value and other relevant information. After the diamond information is entered, "Enter" is selected and the information is stored in the diamond identification table 18, as shown in block 36.

Figure 3:
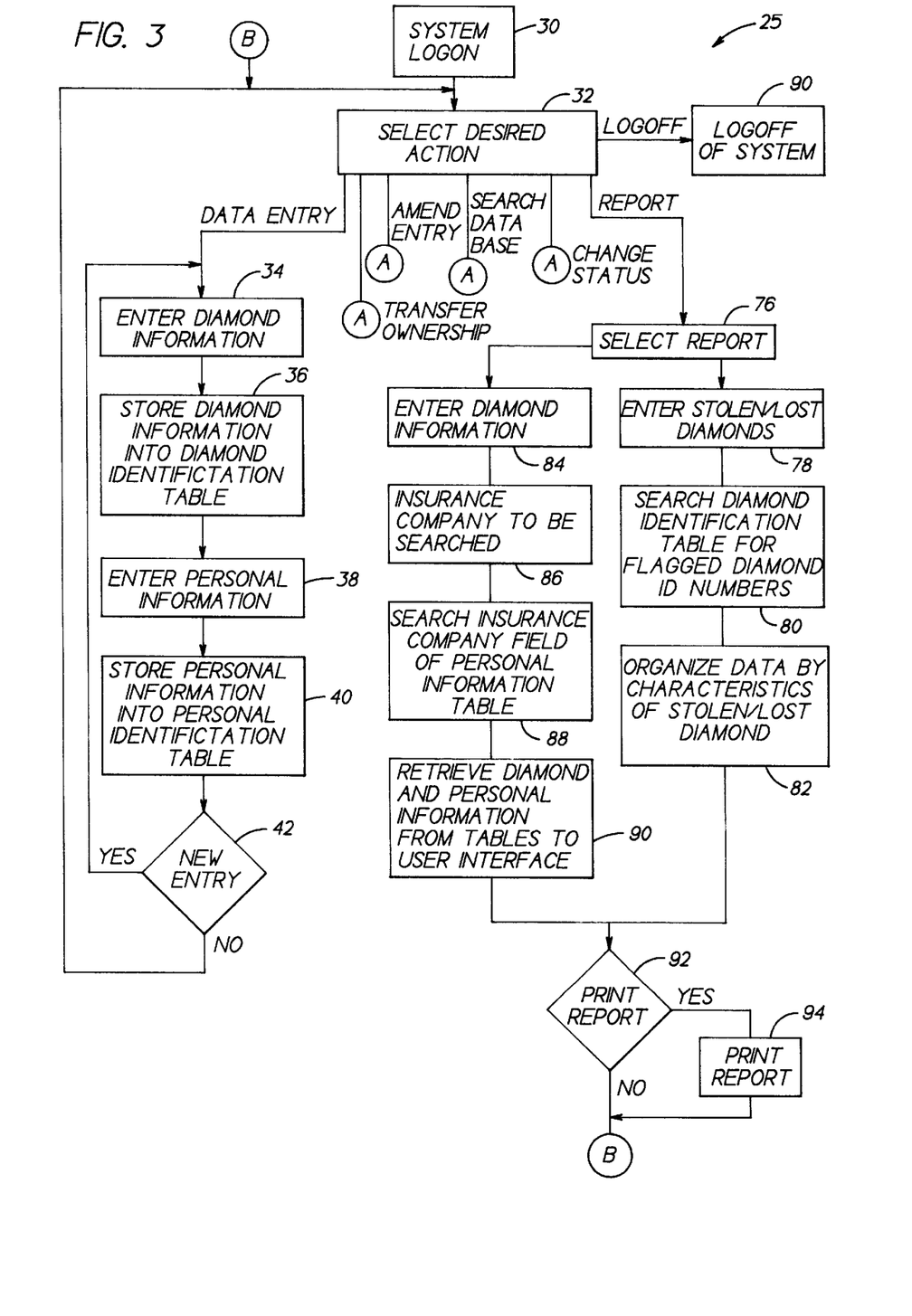
FIG. 3 is a flow diagram of an algorithm used to control the recovery system of the type shown in FIG. 1.
Figure 11:
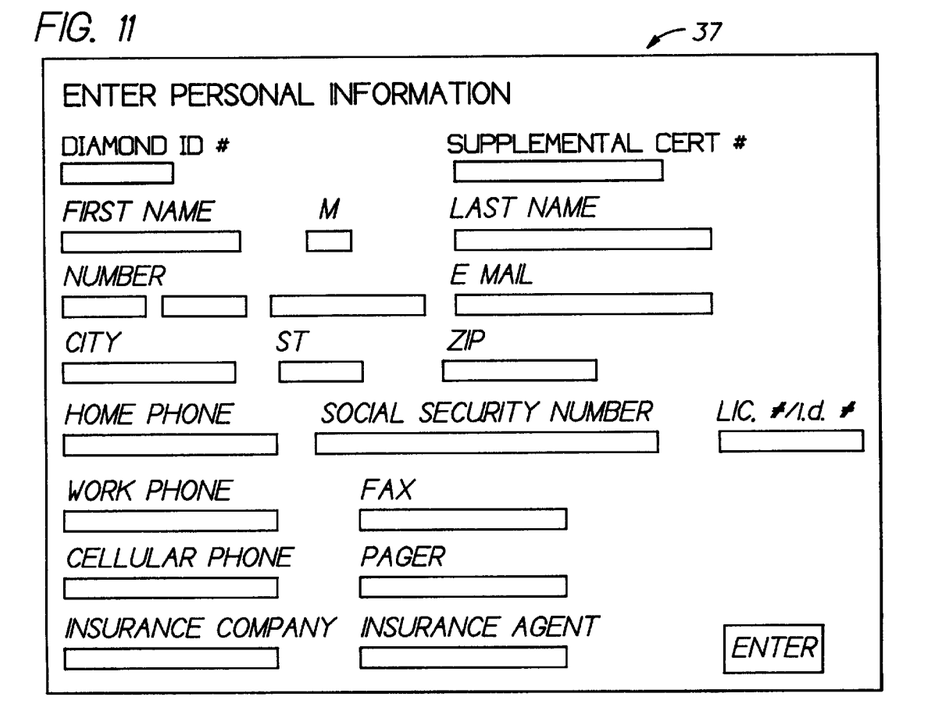
FIG. 11 is a graphical window of the recovery system of FIG. 1 displayed to a system user at block 38 of FIG. 3.

In block 38 of FIG. 3, window 37 of FIG. 11 is then provided to the system user at the user interface 22 which prompts the user to enter the personal information. The user enters the personal information provided by the purchaser. The information that may be entered includes, but is not limited to, the diamond identification number 16; the supplemental diamond certificate number; the license number/I.D. number; the insurance company and agent insuring the diamond; and the name, address, telephone number and facsimile number of the store where the diamond was purchased. The information of the purchaser may also include the purchaser's name, address, home and work telephone number, social security number, pager number, cellular telephone number and e-mail address. After the diamond information is entered, "Enter" is selected and the information is stored in the personal information table 20 (see block 40).

Referring to block 42, the system user is then asked whether another diamond entry wishes to be entered. If so, the user is returned to block 34. If not, the user is returned back to the main menu of block 32.

Figure 12:
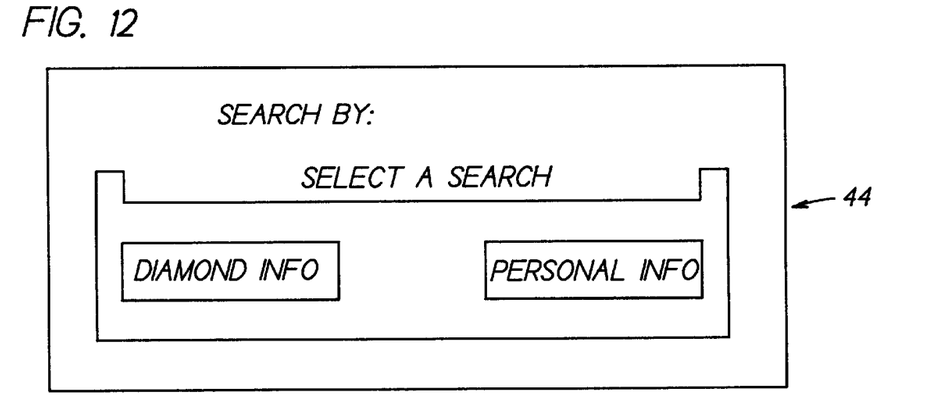
FIG. 12 is a graphical window of the recovery system of FIG. 1 displayed to a system user at block 44 of FIG. 4.
Figure 13:
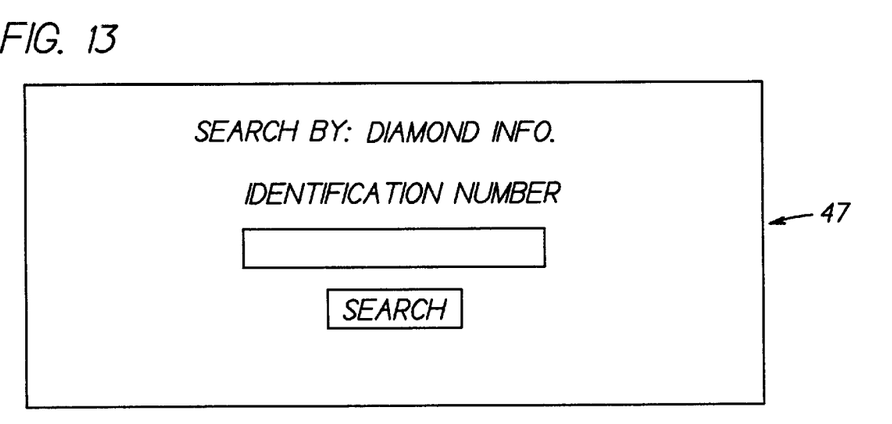
FIG. 13 is a graphical window of the recovery system of FIG. 1 displayed to a system user at block 46 of FIG. 4.

Referring back to the main menu of block 32, if the user selects either "Transfer Ownership", "Amend Entry", "Search Database" or "Change Status", the database 14 is first searched and cross-referenced to verify the diamond 12 is entered into the recovery system 10. As shown in block 44 of FIG. 4, window 45 of FIG. 12 provides the user a choice to search the database 14 by the diamond identification number 16 or by selected personal information. If the user selects to search the diamond identification number, the user is prompted in block 46 to enter the diamond identification number 16 to be searched as shown in window 47 of FIG. 13. In an alternative embodiment, the database may also be searched by the supplemental certificate number. The diamond identification table 18 is searched for all entries having the selected diamond identification number 16 (see block 48) which is then cross-referenced to all entries in the personal information table 20. The most recent or up-to-date entries in each of the tables 18, 20 are displayed to the user. On request by the user for historical information, the processor 24 provides any earlier dated entries of each table 18, 20 to the user interface 22.

Figure 14:
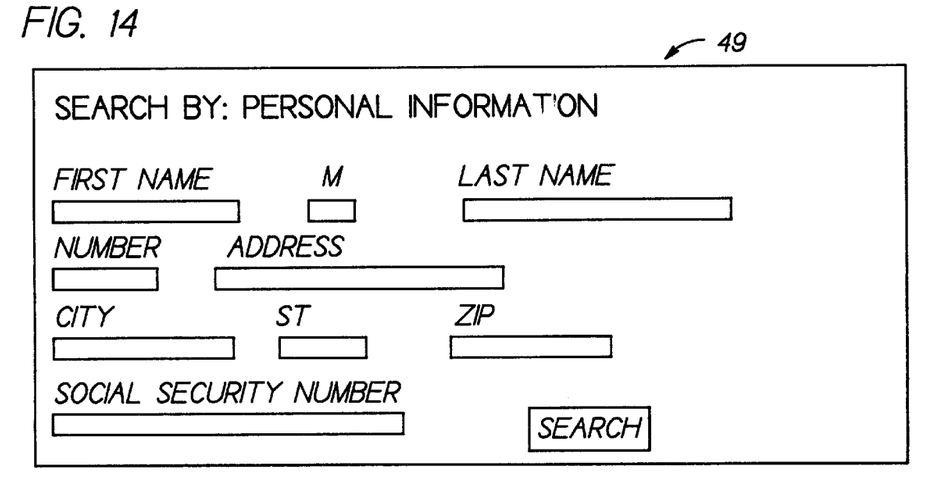
FIG. 14 is a graphical window of the recovery system of FIG. 1 displayed to a system user at block 50 of FIG. 4.

Similarly, if the user selects to search by personal information, as shown in window 49 of FIG. 14, the user is prompted (see block 50) to input selected data of the owner of the diamond 12. The system searches the personal information table 20 (see block 52) for all entries that match the personal information requested. The search routine will search the personal information table 20 by each field of personal information entered which is then cross-referenced to all entries in the diamond identification table 18. The most recent or up-to-date entries in each of the tables 18, 20 are displayed to the user. On request by the user for historical information, the processor 24 provides any earlier dated entries of each table 18, 20 to the user interface 22. If either of the searches are unsuccessful (see block 54), the system will display this fact and prompt the user to return to the main menu at block 32 of FIG. 3.

Figure 4:
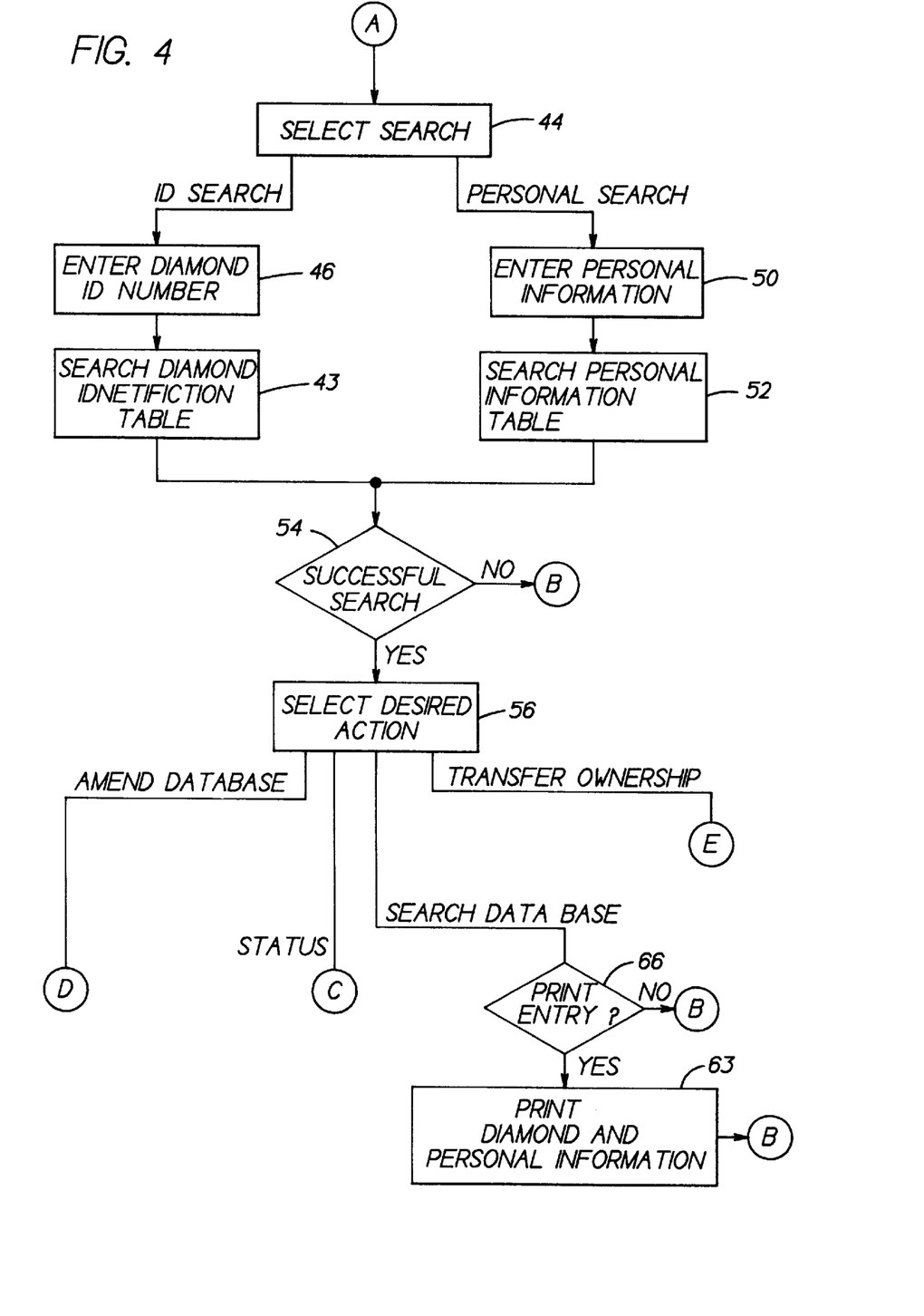
FIG. 4 is a flow diagram of an algorithm used to control the recovery system of the type shown in FIG. 1.
Figure 5:
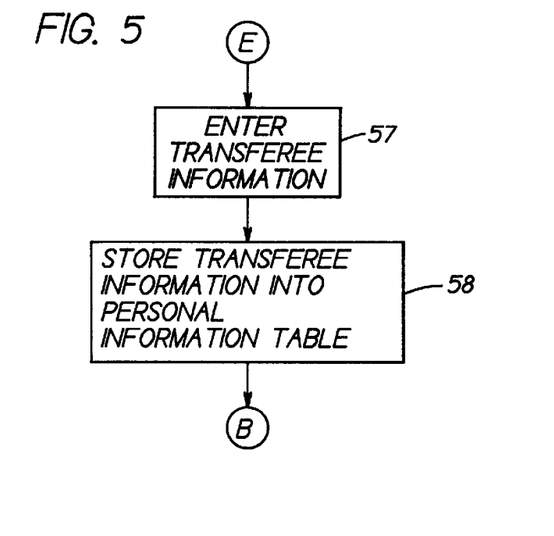
FIG. 5 is a flow diagram of an algorithm used to control the recovery system of the type shown in FIG. 1.

Referring to block 56 of FIG. 4, the user is prompted according to the selected option of the main menu of block 32. If the user selected "Transfer Ownership" in the main menu (see FIG. 9), the user then enters information specific to the individual or business entity of the transferee as shown in block 57 of FIG. 5. The window provided to the system user is similar to window 37 of FIG. 11 when the personal information of the original owner was entered. After the transferee information is entered, "Enter" is selected and the information is stored in the personal information table 20 at a new address as shown in block 58 to provide a history of the ownership of the diamond. The user is then returned to main menu in block 32 (see FIG. 3).

Figure 6:
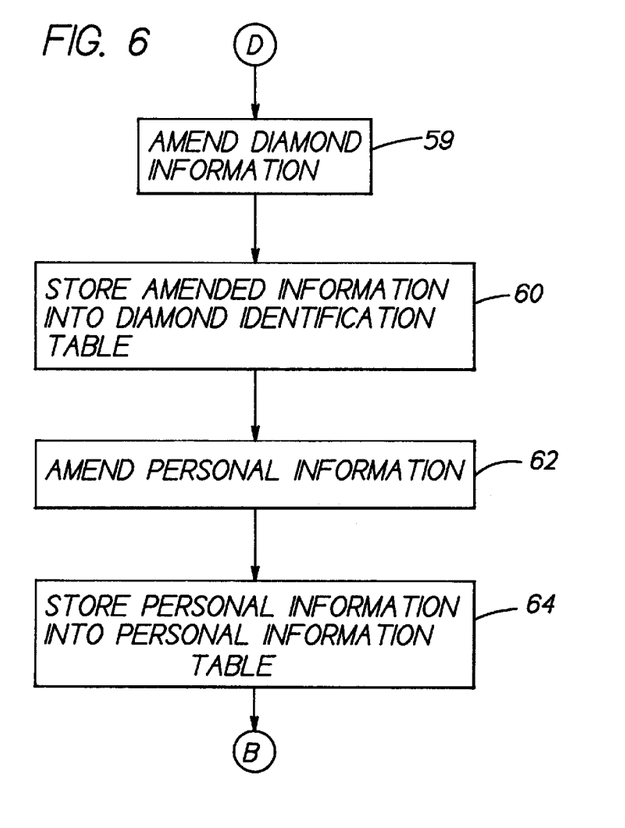
FIG. 6 is a flow diagram of an algorithm used to control the recovery system of the type shown in FIG. 1.

Referring to blocks 59–64 of FIG. 6, if the system user selected "Amend Entry" in the main menu (see FIG. 9), the user then changes and/or adds information to the existing diamond entry. After the diamond entry is changed, "Enter" is selected and the information is stored in the diamond identification table 18 and personal information table 20, respectively, overwriting the original stored data or at a new location in memory in order to maintain a history of the amendments. The user is then returned to main menu in block 32.

Referring to blocks 66, 68 of FIG. 4, if the user selected "Search Database" in the main menu of block 32, the user may print the displayed diamond entry or return to the main menu to return to block 32. After the entry is printed, the system is returned to the main menu.

Figure 7:
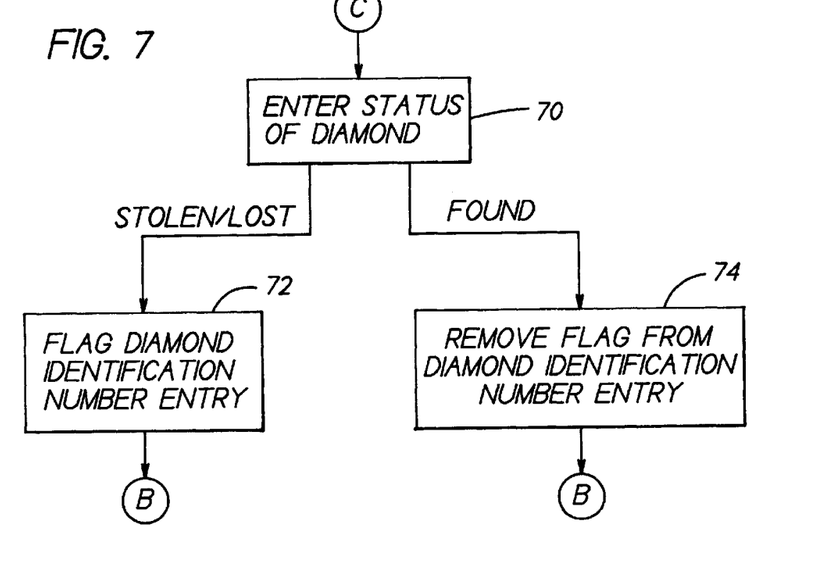
FIG. 7 is a flow diagram of an algorithm used to control the recovery system of the type shown in FIG. 1.
Figure 8:
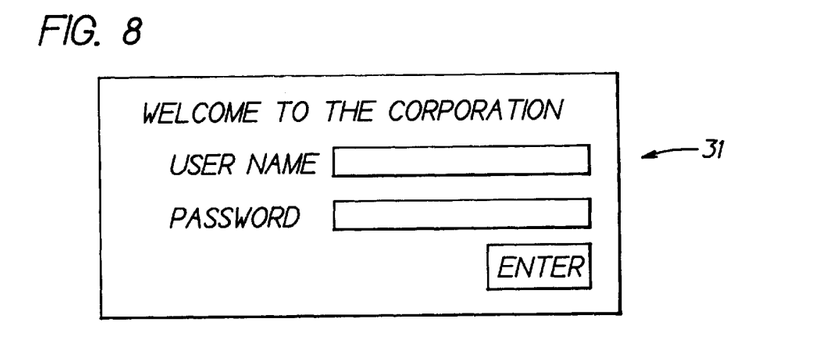
FIG. 8 is a graphical window of the recovery system of FIG. 1 displayed to a system user at block 30 of FIG. 3.
Figure 15:
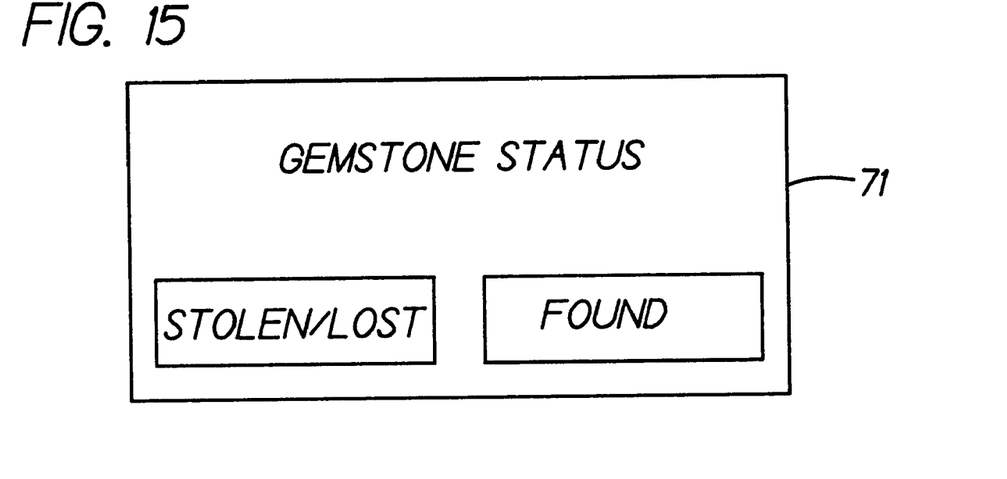
FIG. 15 is a graphical window of the recovery system of FIG. 1 displayed to a system user at block 70 of FIG. 7.

Referring to block 70 of FIG. 7, if the user selected "Change Status" in the main menu 33 of FIG. 9, the system prompts the user to change the status of the diamond entry. Referring to window 71 of FIG. 15, if the user selects "Stolen/Lost", the recovery system 10 flags the diamond entry as stolen or lost (see block 72). If the user selects "Found", the system 10 removes the flag from the diamond entry (see block 74). After toggling the status of the diamond entry, the user is then returned to main menu of block 32.

Figure 16:
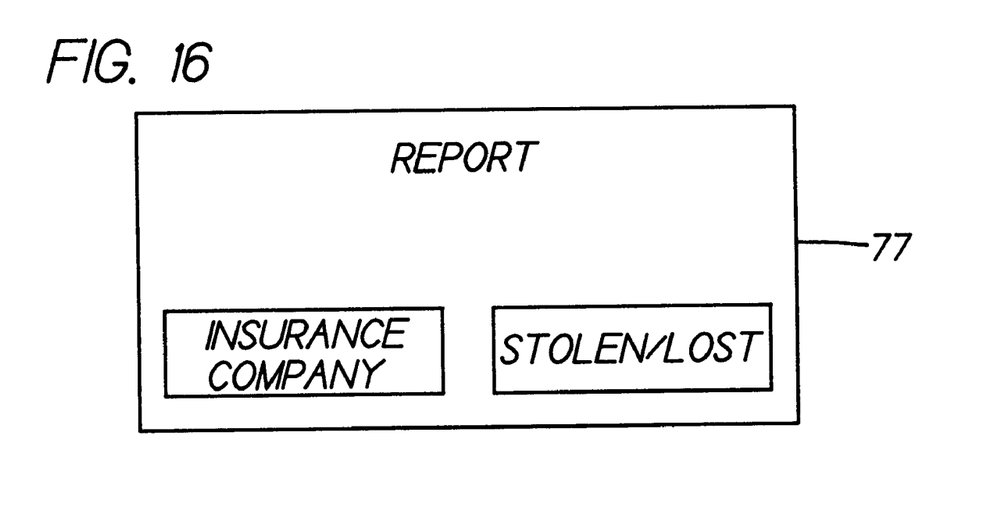
FIG. 16 is a graphical window of the recovery system of FIG. 1 displayed to a system user at block 76 of FIG. 3.

When "Report" is selected in the main menu of block 32, the user is prompted in window 77 of FIG. 16 to select "Insurance Company" or "Stolen/Lost" in block 76 of FIG. 3. When the user selects "Stolen/Lost", in blocks 78–82, the system searches the diamond identification table 18 for the diamond entries that are flagged as being stolen or lost and provides a list of the stolen/lost diamonds. The list may be grouped or categorized by the characteristic of the diamonds (i.e. diamond shape and size). For each diamond listing the diamond identification number 16 is provided. In an alternative form, the diamond entries may be listed in ascending alphanumeric order according to the diamond identification number to enable the police or insurance company to quickly match a diamond having a known identification number to determine its status. In blocks 92 and 94 the user is then prompted to print the listing or return to the main menu of block 32.

When the user selects "Insurance Company", in blocks 84–88 the recovery system 10 prompts the user to enter the name of the insurance company and the system searches the personal information table 20 for all the diamonds 12 insured by that company. In blocks 92 and 94 the system then retrieves the selected information of the identified entries needed to generate the list. The user is then prompted to print the listing or return to the main menu of block 32.

These reports may be generated on a weekly or monthly basis and provided to police, insurance companies and jewelers by electronic transmission or mail. The recovery system may similarly notify the police of any recovered diamonds so they may update their records and also update the police and insurance companies of improved procedures for recovery.

The central headquarters may also provide assistance to owners who report to them of a lost or stolen diamond by reporting theft of the diamond to the local police department to expedite the process of filing a police report.

Referring to block 32 of FIG. 3, when "Log Off" is selected in the main menu, the user is logged off the system (see block 96).

While referred embodiments have been shown and described, various modifications and substitutions may be made thereto without departing from the spirit and scope of the invention. Accordingly, it is to be understood that the present invention has been described by way of illustration and not limitation.

What is claimed is:

1. A computer networking system for recording of gemstones comprising:
   a database for electronically storing a plurality of gemstone entries, each of said gemstone entries including a plurality of parameters relating to a gemstone, said parameters of the gemstone including indicia unique to the gemstone and personal information of an owner of the gemstone, said indicia being inscribed into a surface of each of the gemstones;
   a user interface for displaying at least one parameter of a selected gemstone entries stored in said database and entering gemstone entries for storage in said database; and
   a processor for retrieving gemstone entries selected by said user interface from said database and storing said gemstone entries provided by said user interface to said database in accordance to an algorithm.

2. The system, as defined in claim 1, wherein the processor further flags gemstone entries based on the status of ownership of the gemstone.

3. The system, as defined in claim 2, wherein the status of ownership of a gemstone includes at least one of lost, found, stolen, and change of ownership.

4. The system, as defined in claim 1, wherein the processor, in response to a signal to transfer ownership of a gemstone from said user interface, verifies the gemstone entry in the database and stores information of a transferee of the gemstone provided by said user interface.

5. The system, as defined in claim 1, wherein the processor, in response to a request to amend a selected gemstone entry, retrieves the selected gemstone entry in said database for display at said user interface and stores the amended gemstone entry in said database.

6. The system, as defined in claim 1, wherein the processor, in response to a request to display a parameter of the selected gemstone entry entries, retrieves said gemstone entries in said database that include a parameter by said user interface for display at said user.

7. The system, as defined in claim 6, wherein the parameter includes at least one of the owner of the gemstone, the seller of the gemstone, the transferee of the gemstone, the status of ownership of the gemstone, and a characteristic of the gemstone.

8. The system, as defined in claim 1, wherein the processor, in response to a request to display selected gemstone entry having a selected ownership status, retrieves at least one parameter of said selected gemstone entries for display at said user interface.

9. The system, as defined in claim 1, wherein the parameters of the gemstone entries include the characteristics of the gemstone.

10. The system, as defined in claim 9, wherein the characteristics of the gemstone include the shape and weight of the gemstone.

11. The system, as defined in claim 1, wherein the personal information of the owner of a gemstone includes the name and address of the owner.

12. The system, as defined in claim 1, wherein the personal information of the owner of a gemstone includes the name of the insurer of the gemstone.

13. The system, as defined in claim 1, wherein the personal information of the owner of a gemstone includes the name and address of the store where the gemstone was purchased.

14. The system, as defined in claim 1, wherein the indicia is not visible by the naked eye.

15. The system, as defined in claim 1, wherein the user interface is located remotely from said database.

16. The system, as defined in claim 1, wherein the database comprises:
   a first table for storing parameters of each of said gemstone entries relating to characteristics of the gemstone, said characteristics of the gemstone including said indicia; and
   a second table for storing parameters of each of said gemstone entries relating to said personal information of said owner;
   wherein said parameters of said first and second tables of each gemstone entry includes a unique parameter for cross-referencing each of said gemstone entries of said first and second tables.

17. The system, as defined in claim 1, wherein the parameters of the gemstone entries further include the status of ownership of each respective gemstone.

18. The system, as defined in claim 17, wherein the processor, in response to a signal to change the status of ownership of a gemstone entry from said user interface, verifies said gemstone entry in said database and changes said status of ownership of said gemstone entry.

19. The system, as defined in claim 17, wherein the status of ownership of a gemstone includes at least one of lost, found, stolen, and change of ownership.

20. The system, as defined in claim 1, wherein the user interface includes at least a monitor and a printer for displaying a parameter of a selected gemstone entry.

21. The system, as defined in claim 1, further comprising a second user interface for displaying at least one parameter of a gemstone entry stored in said database.

22. The system, as defined in claim 1, further comprising a second user interface for entering gemstone entries for storage in said database.

23. The system, as defined in claim 22, wherein the second user interface is located remotely from said database.

24. A computer implemented method in a network system of recording information relating to gemstones; said method comprising:

receiving a plurality of gemstone entries from a user interface;

storing electronically the gemstone entries into a database, each of said gemstone entries including a plurality of parameters relating to a gemstone, said parameters of the gemstone including unique indicia parameter and a parameter relating to the owner of the gemstone, wherein said unique indicia is inscribed into a surface of each gemstone; and     retrieving a gemstone entry of a gemstone from said database based on a selected parameter of the gemstone entry for displaying a parameter of the selected gemstone entry at a user interface.

25. The method, as defined in claim 24, further comprising storing a supplemental gemstone entry including information of a transfer of ownership of a corresponding gemstone, said storing the supplemental gemstone entry includes:

receiving a request from the user interface to retrieve the corresponding gemstone entry;

verifying said corresponding gemstone entry is stored in said database;

receiving a parameter relating to a transferee for said supplemental gemstone entry, said transferee parameter including the name and address of the transferee of the corresponding gemstone;

linking said supplemental gemstone entry to said corresponding gemstone entry; and     storing electronically said supplemental gemstone entry in said database.

26. The method, as defined in claim 24, further comprises amending a gemstone entry that includes:

receiving a request from the user interface to retrieve a gemstone entry;

verifying said gemstone entry is stored in said database;

receiving said gemstone entry; and storing electronically said gemstone entry in said database.

27. The method, as defined in claim 24, further comprises displaying selective gemstone entries that includes:

receiving a selected parameter of a gemstone entry; and retrieving gemstone entries having said selected parameter for display at said user interface.

28. The method, as defined in claim 27, wherein the selected parameter includes at least one of the owner of the gemstone, the seller of the gemstone, the transferee of the gemstone, the status of ownership of the gemstone, and a characteristic of the gemstone.

29. The method, as defined in claim 24, further comprises displaying selected parameters of gemstone entries of missing gemstones that includes:

receiving a selected parameter of a gemstone entry; and retrieving gemstone entries that are designated as at least one of lost and stolen for display at said user interface.

30. The method, as defined in claim 24, wherein the parameters of the gemstone entries further include the status of ownership of each respective gemstone.

31. The method, as defined in claim 30, wherein the status of ownership of a gemstone includes at least one of lost, found, stolen, and change of ownership.

32. The method, as defined in claim 30, further comprising flagging a gemstone entry based on the status of ownership of the gemstone.

33. The method, as defined in claim 24, further comprising changing the status of the ownership of a gemstone entry, said changing the status includes:

receiving a request from the user interface to change a gemstone entry;

verifying said gemstone entry is stored in said database;

retrieving selected parameters of the selected gemstone entry;

displaying said gemstone entry to said user interface; and     storing said status of ownership of said selected gemstone entry.

34. The method, as defined in claim 24, wherein the user interface includes at least a monitor and a printer for displaying a parameter of a selected gemstone entry.

35. The method, as defined in claim 24, further comprising retrieving a selected gemstone entry for displaying at least one parameter of a gemstone entry at a second user interface.

36. The method, as defined in claim 24, wherein the user interface is located remotely from said database.

37. The method, as defined in claim 24, further comprising displaying at least one parameter of a gemstone entry stored in said database at a second user interface.

38. The method, as defined in claim 24, further comprising entering gemstone entries for storage in said database at a second user interface.

39. The method, as defined in claim 38, wherein the second user interface is located remotely from said database.

40. A computer implemented method in a network system of recording information relating to gemstones; said method comprising:

inscribing unique indicia onto a surface of each of the gemstones;

receiving a plurality of gemstone entries from a user interface;

storing electronically the gemstone entries into a database, each of said gemstone entries including a plurality of parameters relating to a gemstone, said parameters of the gemstone including unique indicia parameter and a parameter relating to the owner of the gemstone; and     retrieving a gemstone entry of a gemstone from said database based on a selected parameter of the gemstone entry for displaying a parameter of the selected gemstone entry at a user interface.

\* \* \* \* \*

UNITED STATES PATENT AND TRADEMARK OFFICE
CERTIFICATE OF CORRECTION

PATENT NO. : 5,983,238
DATED : November 9, 1999
INVENTOR(S) : Seth P. Becker et al

It is certified that error appears in the above-identified patent and that said Letters Patent is hereby corrected as shown below:

On title page, item [54], delete"GEMSTONS" and insert therefor --GEMSTONE--
Column 1, in the title of the patent, delete"GEMSTONS" and insert therefor --GEMSTONE--
Column 5, line 25 delete "a" between "common" and"link"
Column 10, line 5 delete "entry" between "gemstone" and "entries"

Signed and Sealed this

Thirteenth Day of March, 2001

*Attest:*

NICHOLAS P. GODICI

*Attesting Officer*     *Acting Director of the United States Patent and Trademark Office*